(12) United States Patent
Harris et al.

(10) Patent No.: US 7,696,174 B2
(45) Date of Patent: Apr. 13, 2010

(54) SHORT BIO-ACTIVE PEPTIDES FOR CELLULAR AND IMMUNOLOGICAL MODULATION

(75) Inventors: Scott M. Harris, Seattle, WA (US); Lijuan Zhang, Kenmore, WA (US); Timothy J. Falla, Woodinville, WA (US)

(73) Assignee: Helix Biomedix, Inc., Bothell, WA (US)

( * ) Notice: Subject to any disclaimer, the term of this patent is extended or adjusted under 35 U.S.C. 154(b) by 0 days.

(21) Appl. No.: 12/005,653

(22) Filed: Dec. 27, 2007

(65) Prior Publication Data

US 2008/0206160 A1    Aug. 28, 2008

Related U.S. Application Data

(60) Provisional application No. 60/878,849, filed on Jan. 5, 2007.

(51) Int. Cl.
*A61K 38/08* (2006.01)
*A61K 31/74* (2006.01)

(52) U.S. Cl. ..................... 514/15; 424/78.06

(58) Field of Classification Search ........................ None
See application file for complete search history.

(56) References Cited

U.S. PATENT DOCUMENTS

| 5,034,510 | A * | 7/1991 | Shiba et al. ............... 530/326 |
| 5,763,576 | A | 6/1998 | Powers ...................... 530/330 |
| 6,492,326 | B1 | 12/2002 | Robinson et al. .............. 514/2 |
| 6,875,744 | B2 * | 4/2005 | Owen ........................ 514/16 |
| 7,041,506 | B2 | 5/2006 | Campbell et al. ........... 435/402 |
| 2003/0175745 | A1 | 9/2003 | Dean et al. .................... 435/6 |
| 2004/0009911 | A1 | 1/2004 | Harris et al. ................ 514/12 |
| 2005/0085422 | A1 | 4/2005 | Georgiades ................. 514/13 |
| 2005/0288229 | A1 | 12/2005 | Sindrey et al. .............. 514/16 |
| 2006/0046271 | A1 | 3/2006 | Hallahan .................... 435/7.1 |
| 2007/0021347 | A1 | 1/2007 | Khan et al. ................. 514/16 |
| 2007/0166267 | A1 | 7/2007 | Majewski et al. ......... 424/70.14 |
| 2007/0183970 | A1 | 8/2007 | Goldenberg et al. ....... 424/1.49 |
| 2007/0224150 | A1 | 9/2007 | Chung ................... 424/70.14 |

FOREIGN PATENT DOCUMENTS

| CA | 2276542 | 12/2000 |
| DE | 102004050563 A1 | 4/2006 |
| EP | 0858808 A2 | 8/1998 |
| EP | 1004595 A2 | 5/2000 |
| EP | 1 634 576 A1 | 3/2006 |
| EP | 1 815 843 A2 | 8/2007 |
| WO | WO 89/10099 A1 | 11/1989 |
| WO | WO-90/12866 | * 11/1990 |
| WO | WO95/28832 A1 | 11/1995 |
| WO | WO02/079408 A2 | 10/2002 |
| WO | WO 2006/042625 A2 | 4/2006 |
| WO | WO 2006/053688 A1 | 5/2006 |
| WO | WO 2006/108963 A1 | 10/2006 |

OTHER PUBLICATIONS

Shiba, 1988, Tetrahedron, 44, 787-803.*
Shiba, 1988, Tetrahedron Letters, 28, 4705-4706.*
Lee, 2004, Wound Rep. Reg., 12, 351-358.*
Schultz et al., Extracellular matrix: review of its roles in acute and chronic wounds, *World Wide Wounds* (www.worldwidewounds.com) (Aug. 2005).
Katayama et al., A pentapeptide from type I procollagen promotes extracellular matrix production, *Journal of Biological Chemistry* 268:9941-9944 (1993).
Greenbaum et al., Chemical approaches for functionally probing the proteome, *Molecular and Cellular Proteomics* 1:60-68 (2002).
Krstenansky et al., Probing proteinase active sites using oriented peptide mixture libraries—ADAM-10, *Letters in Drug Design and Discovery* 1:6-13 (2004).
Tran et al., Extracellular matrix signaling through growth factor receptors during wound healing, *Wound Repair and Regeneration* 12:262-268 (2004).
Maquart et al., [Regulation of cell activity by the extracellular matrix: the concept of matrikines], *Journal de la Société de biologie* 193:423-428 (1999) Abstract Only.
Duca et al., Elastin as a matrikine, *Critical Reviews in Oncology/Hematology* 49:235-244 (2004).
Arul et al., Biotinylated GHK peptide incorporated collagenous matrix: a novel biomaterial for dermal wound healing in rats, *Journal of Biomedical Materials Research Part B: Applied Biomaterials* 73:383-391 (2005).
Tran et al., Matrikines and matricryptins: implications for cutaneous cancers and skin repair, *Journal of Dermatological Science* 40:11-20 (2005).
Heilborn et al., the cathelicidin anti-microbial peptide LL-37 is involved in re-epithelialization of human skin wounds and is lacking in chronic ulcer epithelium, *Journal of Investigative Dermatology* 120:379-389 (2003).
Bessalle et al., Structure-function studies of amphiphilic antibacterial peptides, *J. Med. Chem.* 36:1203-1209 (1993).

(Continued)

*Primary Examiner*—Andrew D Kosar
*Assistant Examiner*—Satyanarayana R Gudibande
(74) *Attorney, Agent, or Firm*—Howrey LLP (57) ABSTRACT

Peptides having four to fourteen residues are disclosed that possess biological activity. These peptides constitute short fragments of the peptide HB-107 (SEQ ID NO:1), which itself is a fragment of the antimicrobial protein cecropin B, and exhibit cell stimulatory, migratory and anti-inflammatory properties. As keratinocytes are especially sensitive to these effects, the disclosed peptides comprise a useful agent for the medical treatment of injury to the skin, such as from diabetic ulcers. The peptides also are effective in preventing and reversing skin surface damage resulting from various environmental insults. Importantly, the therapeutic effects of the peptides manifest at concentrations equal to or greater than those of peptide HB-107, and thus represent a less expensive, more versatile means for developing effective therapies. Methods for the production and use of these peptides are also disclosed.

18 Claims, 3 Drawing Sheets

OTHER PUBLICATIONS

Oh et al., Design, synthesis and characterization of antimicrobial pseudopeptides corresponding to membrane-active peptide, *J. Peptide Res.* 54:129-136 (1999).

Lee Pha et al. (2004), HB-107, a nonbacteriostatic fragment of the antimicrobial peptide cecropin B, accelerates murine wound repair, *Wound Rep. Reg.* 12:351-358.

Reed Wa et al. (1992), Enhanced in vitro growth of murine fibroblast cells and preimplantation embryos cultured in medium supplemented with an amphipathic peptide, *Mol. Rep, Develop.* 31:106-113.

Andreu D et al. (1985), N-terminal analogues of cecropin A: synthesis, antibacterial activity, and conformational properties, *Biochemistry* 24:1683-1688.

Morgan K et al. (1992), Identification of an immunodominant B-cell epitope in bovine type II collagen and production of antibodies to type II collagen by immunization with a synthetic peptide representing this epitope, *Immunology* 77:609-616.

Degryse B et al. (2005), Domain 2 of the urokinase receptor contains an integrin-interacting epitope with intrinsic signaling activity, *J. Biol. Chem.* 280:24792-24803.

Wu W-J and Raleigh DP (1998), Local control of peptide conformation: stabilization of *cis* proline peptide bonds by aromatic proline interactions, *Biopolymers* 45:381-394.

Kessler E and Yaron A (1973), A novel aminopeptidase from *Clostridium histolyticum, Biochem. Biophys. Res. Comm.* 50:405-412.

Wunsch E et al. (1971), Zur spezifitat der kollagenase, *Hoppe-Seyler's Zeitschrift Fuer Physiologische Chemie* 352:1568-1579.

\* cited by examiner

Fig. 1

| SEQ ID NO | HB No. | | | | | | | | | | | | | | | | | | |
|---|---|---|---|---|---|---|---|---|---|---|---|---|---|---|---|---|---|---|---|
| 1 | 107 | M | P | K | E | V | F | L | K | I | E | K | M | G | R | N | I | | R | N |
| 2 | 1059 | | | | | | | | | | | | | | | | | | | N |
| 3 | 1061 | | | | | | | | | | | | | | | | | | R | N |
| 4 | 1062 | | | | | | | | | | | | | | | | | | R | |
| 5 | 1071 | | | | | V | | | | | | | | | | | | | | |
| 6 | 1072 | | | | | | F | L | K | | E | K | M | G | | | | | | |
| 7 | 1074 | | | | | V | | L | K | | E | K | M | G | | | | | | |
| 8 | 1076 | | | K | E | V | F | L | K | | E | K | | G | | | | | | |
| 9 | 1057 | | | K | E | V | | L | K | | E | K | M | G | | | | | | |
| 10 | 912 | M | P | K | E | | F | L | K | | E | K | M | G | R | N | | | R | N |
| 11 | 801 | M | P | K | | | | | | | E | K | M | G | | | | | | |
| 12 | 802 | M | P | K | | | | | | | E | K | | | | | | | | |
| 13 | 1056 | | | | | | | | | | | | | | | | | | | |
| 14 | 1060 | | | | | | | | L | | E | K | M | G | R | N | I | | R | N |
| 15 | 1410 | | P | K | E | | | | K | | | | | | R | N | | | R | N |

SHORT BIO-ACTIVE PEPTIDES FOR CELLULAR AND IMMUNOLOGICAL MODULATION

This application claims the benefit of priority to U.S. Provisional Application No. 60/878,849, filed Jan. 5, 2007, which is herein incorporated by reference in its entirety.

FIELD OF THE INVENTION

The invention relates to peptides having biological and therapeutic activity. Particularly, the invention relates to short peptides having four to fourteen contiguous amino acid residues of SEQ ID NO:1 that exhibit proliferative, migratory and anti-inflammatory activities towards cells such as keratinocytes. The invention is further related to methods of using of these peptides to treat various insults affecting the skin and other related body surfaces such as the oral cavity.

BACKGROUND OF THE INVENTION

Skin epidermis consists of four to five stratified layers, all of which comprise mostly keratinocytes; other cell types such as fibroblasts also populate the epidermis. Keratinocytes originate from the bottom-most, basal layer of the epidermis, and gradually migrate to the most exterior portion of the skin, where they become cornified and eventually slough. During this migration, keratinocytes differentiate to express the enzymes and structural proteins necessary for cornification (Presland and Dale, 2000). Given their prominent role in forming the epidermis, keratinocytes represent a main target for treating damaged skin.

Keratinocytes are also a main constituent of mucosal tissues that are continuous with the epidermis (Presland and Dale, 2000). Such tissue lacks the impermeable, cornified layer of the epidermis, and forms the inner-lining surfaces associated with the mouth, nose, throat, ear, anus and genitalia. Similar to the skin, mucosal surfaces are important for preventing entry of infectious agents into the body; thus, injury to either of these tissue types may compromise the health of an individual.

Skin and mucosal tissue damage occurs when the epidermal layer is breached, such as from a laceration, burn or blister. Injury can also involve crushing or bruising, which involves tissue damage without concurrent fissure of the epidermis. Skin infections as well as certain chronic illnesses such as cancer and autoimmune diseases can also exact a toll on epidermal surfaces. Ulcers, such as those affecting diabetics or those associated with pressure sores, are another form of skin damage; these wounds are often quite intractable, being inflamed, prone to infection, and requiring a lengthy healing process. It is generally posited that the persistence of an ulcer, or any other chronic wound, is due to a failure of cellular processes involved in healing, such as cell signaling (Enoch and Price, 2004; Sweitzer et al., 2006). One failure is the inability to epithelialize the lesion—keratinocytes at the wound border, though able to proliferate, do not mobilize to cover the sore (Enoch and Price, 2004). In relation to diabetic ulcers, another failure is the lack of certain signaling molecules; this deficiency which may preclude the remodeling processes that are necessary for orchestrating wound closure (Sweitzer et al., 2006).

Other forms of epidermal damage are subtle and result over a long period of time, eventually compromising skin function in the face of acute injury; wound healing is extended in time and can be imperfect (e.g. scar formation). Cosmetic problems such as wrinkling, dryness, thinning, sagging and greater susceptibility to bruising are usual outward signs of such maladies. Not surprisingly, these signs of wear-and-tear are usually associated with aging, but can also occur prematurely due to prolonged exposure to damaging agents such as ultraviolet rays (photoaging). The photoreactive processes induced by sunlight can contribute to reduced skin thickness and elasticity, as well as increased skin toughening (Pelicci, 2004; Fisher et al., 2002).

Healing of acute skin and mucosal wounds is orchestrated, in part, through the activation of basal keratinocytes, which follow a path of proliferation, migration and differentiation to effect wound closure. This process is accompanied by an array of remodeling activities at the injury site (Enoch and Price, 2004). Keratinocytes located at the wound perimeter proliferate and migrate to form a single layer over the wound in a process referred to as epithelialization. Further proliferation and differentiation of the keratinocytes establishes an epidermal layer comprising the normal stratified layers. Inflammatory processes may facilitate wound healing; infiltrating monocytes fight infection and also release factors that stimulate wound epithelialization. However, inflammatory processes can also aggravate healing; for example, fibrin deposition by macrophages contributes to scarring. So long as antiseptic conditions are maintained, it has been shown that epidermal wound closure occurs faster and with less scarring when immune involvement is curtailed (Martin and Leibovich, 2005). It is with these insights in mind that modes for down-modulating inflammation at epidermal lesions are currently contemplated.

Several factors have been shown to spur epithelialization by keratinocytes during wound healing in skin and associated mucosal tissues, including epidermal growth factor (EGF), basic fibroblast growth factor (bFGF), keratinocyte growth factor (KGF), and platelet-derived growth factors (PDGFs) (Enoch and Price, 2004). Interestingly, several antimicrobial proteins that are present on skin and mucosal surfaces are also known to play a role in stimulating the cell proliferation and migration required for healing epidermal wounds (Shaykhiev et al., 2005; Braff and Gallo, 2006; Zhang and Falla, 2006).

With the knowledge that certain growth factors are naturally engaged during wound healing, work has been directed towards developing growth factor-based methods for treating wounds, especially those that are generally chronic. For example, treatment of diabetic ulcers with PDGF-BB (Mustoe et al., 1994; Steed, 1995) has gained FDA approval. However, most attempts employing such a strategy have failed to achieve clinically significant results, due in part to difficulties associated with use of therapeutic proteins. One problem relates to the inefficient delivery of growth factors to wound sites; topical application of these proteins only permits exposure of exterior, mostly dead tissue to the therapeutic protein. Other drawbacks relate to the high lability and poor retention of growth factor proteins after delivery to the wound site.

Difficulties with the use of growth factors and other proteins to treat epidermal wounds are related to the large size of the proteins involved. Widespread use of growth factor therapies also suffers from the complexity and high costs associated with preparing large proteins. Therefore, as it concerns the use of protein factors in wound healing regimens, less expensive and more effective preparations are presently sought. Short peptides that bear the activity of the larger proteins from which they are derived (i.e. parent protein) fill this need. Previous examples of such short peptides have been reported (U.S. Pat. Nos. 6,861,406 and 6,693,077; Lee et al., 2004). Besides the immediate benefits of less expensive, more simple production, handling, and manipulation, small bio-active peptides are also better absorbed and retained by wound tissue. The advanced absorption characteristics of short bio-active peptides also make them a viable option for uses beyond the care of acute and chronic lesions, such as for treatment of the skin problems associated with old age and sun exposure.

SUMMARY OF THE INVENTION

The present invention is drawn toward short bio-active peptides that are useful for promoting wound healing in mammals. The wounds preferably targeted by the isolated peptides are those affecting the skin and associated mucosal surfaces. Though not to be limited to any particular mechanism, the inventive peptides are able to effect wound healing by stimulating cell proliferation and migration, as well as by inhibiting inflammation, which can impair optimal healing processes. The inventive peptides are useful in both in vitro and in vivo manners, and are able to induce the aforementioned activities in keratinocytes.

One embodiment of the present invention is drawn toward isolated peptides that contain four to fourteen contiguous amino acid residues of SEQ ID NO:1. Such peptides represent short fragments of the peptide HB-107. The isolated peptides may contain either L- or D-enantiomeric forms of amino acids, or combination thereof. According to yet another embodiment of the invention, the isolated peptides may be conjugated to a carrier protein, or modified via amidation or lipidation. These additions enhance the bio-activity of the peptides when applied to skin and wounds thereof.

According to certain preferred embodiments of the current invention, the isolated peptides may contain a methionine, valine, lysine, or glutamate amino acid residue at the amino terminus. The isolated peptides may also have a lysine, valine, glycine, or asparagine amino acid residue at the carboxy terminus. In other preferred embodiments, the isolated peptides may comprise SEQ ID NO:3, SEQ ID NO:6, or SEQ ID NO: 12. Specific embodiments of the isolated peptides are SEQ ID NO:2, 3, 5, 6, 7, 8, 9, 10, 11, 12 and 15, all of which show one or more stimulatory activities towards cell proliferation, migration, and anti-inflammation. Of these specific peptides, SEQ ID NO:2, 3, 5, 6, 7, 9, 10, 11 and 12 all possess cell proliferative activity; and of these peptides, SEQ ID NO:2, 3, 5, 6 and 9 exhibit the strongest proliferative activity. Peptides SEQ ID NO:3 and 6 possess both cell proliferative and migratory activities. SEQ ID NO:12 possesses both cell proliferation and anti-inflammation activities, whereas SEQ ID NO:8 and 15 possess cell anti-inflammation activity.

Another embodiment of the present invention is drawn toward compositions which contain a pharmaceutically acceptable carrier and one or more of the aforementioned peptides. The peptide in such compositions preferably ranges in concentration from about 0.1 µg/mL to about 20 µg/mL, or from about 0.1 µg/mL to about 50 µg/mL. Preferred forms of the composition are aerosols, emulsions, liquids, lotions, creams, pastes, ointments, powders and foams.

The present invention is also directed towards methods of using the aforementioned compositions for healing wounds in mammals. Typically, the treatment method entails administering an effective amount of peptide-containing compositions to wounds, especially those of the skin (epidermis) and associated mucosal tissues, for an effective amount of time. Such wounds include abrasions, blisters, burns, lacerations, ulcers, bruises, rashes, scars, and the effects of aging and environmental exposure.

DETAILED DESCRIPTION OF THE INVENTION

U.S. Pat. Nos. 5,962,410 and 5,861,478 provide disclosures useful for understanding the present invention and are herein incorporated by reference in their entirety. The invention is directed towards short, bio-active peptides that, for example, are derived from the peptide HB-107 (SEQ ID NO:1), and methods of their use. Peptide HB-107 itself constitutes a fragment of cecropin B, which is an antimicrobial protein present in a species of moth. Although HB-107 does not display the bacteriostatic effects of the protein from which it is derived, it does display epidermal wound healing qualities (Lee at al., 2004).

The peptides of the present invention display activities that are important for upregulating healing processes in epidermal tissues such as skin and associated mucosa (e.g. oral cavity). Not to be limited to any particular mechanism, these activities are drawn towards keratinocytes, the epithelial cells responsible for wound closure (i.e. epithelialization) and development of epidermal surfaces. The specific activities that the inventive peptides display towards keratinocytes that are of direct relevance to wound healing are stimulation of cell proliferation and migration, as well as the ability to downregulate inflammatory signaling by the keratinocytes. Though HB-107 is capable of inducing all of these activities in keratinocytes, quite surprisingly, the peptides of the present invention do so at levels equal to or greater than HB-107. These results are both surprising and significant, since the inventive peptides are only 26%-74% the length of HB-107.

Because of this size differential, the peptides of the current invention are easier and thus less expensive to prepare compared to production of HB-107 and full-size proteins such as PDGF-BB. Also in contrast to larger peptides, the disclosed peptides are solubilized, manipulated (e.g. chemical modification) and stored in a more straightforward manner. Their ease-of-handling enables a greater number of drug delivery options, such as the vehicle to be used and how it is to be applied. The size and greater solubility of the inventive peptides permit their increased healing potency through increased absorption and retention at the wound site; local keratinocytes and other cells are exposed to higher concentrations of the peptides for longer periods of time.

The biological activities elicited by the peptides of the present invention are cell proliferation and migration, as well as the inhibition of inflammation. The former two processes play a large role in mediating the wound healing function of the peptides. The peptides are able to first, stimulate migration of keratinocytes bordering the wound edge, and second, stimulate proliferation of these cells so as to create a new epidermal layer over the injury site. The third activity, inhibiting inflammation, is achieved via the disclosed peptides' negative effect on secretion of the cytokine interleukin-6 (IL6) by cells at the wound. IL6 has been shown to be a released by epidermal keratinocytes in response to factors associated with tissue damage (Sugawara et al., 2001); this cytokine signals for immune cell infiltration into the wound, a process which can actually aggravate healing and cause scarring (Martin and Leibovich, 2005; Liechty, 2000). Though inflammation is important to prevent wound infection, the provision of good antiseptic practices during standard wound care negates any drawbacks that may be associated with blocking inflammation. Though the above activities are likely those through which the invention effects wound healing, it is noted that the application is not limited by any one particular set of biological mechanisms.

With respect to inducing cell proliferation and migration, the peptides SEQ ID NO:3 (HB-1061) and SEQ ID NO:6 (HB-1072) are preferred. These peptides produce significant increases in cell proliferation compared to induction by HB-107, but yet are shorter than HB-107 (refer to Examples 1 and 2). They are also just as capable as HB-107 in inducing cell migration. The peptides SEQ ID NO:8 and SEQ ID NO:12 are preferred with respect to induction of cellular anti-inflammatory activity (refer to Example 3).

The inventive peptides also exhibit salutary effects towards problems associated with aging skin, or skin that has been highly exposed to damaging agents such as solar radiation. The short peptides by themselves unaltered, or via chemical modification and/or specialized delivery, can be made to absorb through the epidermis to effect processes counter to those that cause skin thinning, wrinkles, fragility and roughening/hardening. A major mode by which the invention stimulates skin preservation is through the peptides' positive effect toward keratinocyte growth. As these cells are the main component of epidermal surfaces and are diminished in aged and damaged skin (Enoch and Price, 2004), replenishment thereof by peptide stimulation is expected to reverse the aforementioned problems. IL6 expression is implicated in processes underlying the abnormal thickening of the epidermis in patients with certain autoimmune problems (Sato et al., 2001; Oyama et al., 1998); the inventive peptides can block such an inflammation-related outcome by inhibiting IL6 expression.

Peptides

Solely as a guiding point, the inventive peptides can be derived from the HB-107 fragment (Table 1) of the moth cecropin B protein. The metabolic features associated with these peptides are their capability of inducing cell proliferation, migration, and/or anti-inflammatory activities. All the inventive peptides share the common feature of having four to fourteen contiguous amino acid residues of HB-107 (SEQ ID NO:1). Therefore, peptides of the invention may consist of four, five, six, seven, eight, nine, ten, eleven, twelve, thirteen or fourteen contiguous amino acid residues of HB-107 (SEQ ID NO:1).

Aside from having the above amino acid compositions, the above-described peptides may additionally contain the following amino acids (full name/three letter abbreviation/single letter abbreviation): alanine/ala/A, arginine/arg/R, asparagine/asn/N, aspartate/asp/D, cysteine/cys/C, glutamine/gln/Q, glutamate/glu/E, glycine/gly/G, histidine/ his/H, isoleucine/ile/I, leucine/leu/L, lysine/lys/K, methionine/met/M, phenylalanine/phe/F, proline/pro/P, serine/ser/S, threonine/thr/T, tryptophan/trp/W, tyrosine/tyr/Y and valine/val/V. These amino acid residues are characterized as follows: aliphatic (alanine, glycine, isoleucine, leucine, proline, valine), aromatic (phenylalanine), tryptophan, tyrosine), acidic (aspartate, glutamate), basic (arginine, histidine, lysine), hydroxylic (polar) (serine, threonine), sulphur-containing (polar) (cysteine, methionine), and amidic (asparagine, glutamine). Non-standard amino acid residues may also be incorporated into the disclosed peptide including, but not limited by, selenocysteine, pyrolysine and various cyclic forms of amino acids.

The following peptides are non-limiting examples of the present invention and are shown for illustrative purposes (Table 1).

TABLE 1

Peptides of the current invention.

| SEQ ID NO: | Peptide | Sequence |
|---|---|---|
| 1 | HB-107 | MPKEKVFLKIEKMGRNIRN |
| 2 | HB-1059 | EKMGRNIRN |
| 3 | HB-1061 | MGRNIRN |
| 4 | HB-1062 | GRNIRN |
| 5 | HB-1071 | VFLKIEKMG |
| 6 | HB-1072 | KIEKMG |
| 7 | HB-1074 | VFLKIEK |
| 8 | HB-1076 | KEKVFLKIE |
| 9 | HB-1057 | KIEKMGRNIRN |
| 10 | HB-912 | MPKEKVFLKIEKMG |
| 11 | HB-801 | PKEKV |
| 12 | HB-802 | MPKEK |
| 13 | HB-1056 | LKIEKMGRNIRN |
| 14 | HB-1060 | KMGRNIRN |
| 15 | HB-1410 | PKEK |

The peptides SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:15 are examples of peptides associated with one or more of the activities (proliferative, migratory, anti-inflammatory) described above. The peptides SEQ ID NO:2, SEQ ID NO:3, SEQ ID NO:5, SEQ ID NO:6, SEQ ID NO:7, SEQ ID NO:9, SEQ ID NO:10, SEQ ID NO:11 and SEQ ID NO:12 are examples of peptides that can induce cell proliferation. The peptides SEQ ID NO:3 and SEQ ID NO:6 are examples of peptides that can induce cell proliferation and migration. The peptide SEQ ID:12 is an example of a peptide that displays both proliferative and anti-inflammatory activities. The peptides SEQ ID NO:8 and SEQ ID NO:15 are examples of peptides having anti-inflammatory activity.

Each of the above-described peptides can comprise L- or D-amino acid enantiomers, either containing residues of one enantiomeric form or a combination of both forms. The peptides may be further augmented or modified, either chemically or enzymatically, as described in the following non-limiting examples. The carboxy-terminus of the peptides can be acidic (—COOH) or be amidated (e.g. —CONH$_2$, —CONHR, or —CONR$_2$). Amidation of the carboxy-terminus may render the inventive peptides less susceptible to protease degradation and increase their solubility compared to the free acid forms, therefore providing heightened therapeutic potency. The peptides may also be lipidated which may provide for enhanced skin penetration. Peptide modifications may be made such that a hydrogen of the N-terminal amino group is replaced, a hydroxyl group (OH) of the C-terminal carboxylic group is replaced, the entire N-terminal amino group is replaced, or the entire C-terminal carboxylic group is replaced. One or more of the molecular bonds that link the amino acids of each peptide may be a non-peptide bond. Such non-peptide bonds include, but are not limited to, imido, ester hydrazine, semicarbazoide and azo bonds.

A variety of modifications can be made to the peptides as long as the characteristic proliferative, migratory and anti-inflammatory activities thereof are retained. Some modifications may be used to increase the potency of the peptide, while other modifications may facilitate peptide handling. Peptide functional groups that may typically be modified include hydroxyl, amino, guanidinium, carboxyl, amide, phenol, imidazol rings or sulfhydryl. Typical, non-limiting reactions of these groups include the following: acetylation of hydroxyl groups by alkyl halides; esterification, amidation or hydrogenization (i.e. reduction to alcohol) of carboxyl groups; deamidation, acylation, alkylation, arylation of amino groups (e.g. primary amino group of the peptide or the amino group of lysine residues); halogenation or nitration of tyrosine phenol groups.

Peptides may be conjugated to soluble or insoluble carrier molecules to modify their solubility properties as needed and to increase the local concentrations of peptides in targeted tissues. Examples of soluble carrier molecules include polymers of polyethyleneglycol (PEG) and polyvinylpyrrolidone; examples of insoluble polymers include silicates, polystyrene, and cellulose. Peptides may also be micro-encapsulated to enhance their stability during and after therapeutic application; typically, polyester and PEG microspheres are used to encapsulate and stabilize the peptides.

Various methods of preparing microspheres for peptide encapsulation may be employed depending upon the hydrophilic or hydrophobic nature of the peptide composition to be encapsulated. Examples of protocols for such methods are found in Wang HT et al. (1991, *J. Control. Release* 17:23-25) and U.S. Pat. No. 4,324,683, both of which are incorporated herein in their entirety. In vitro peptide release studies may be performed to determine the relative availability of the peptide after it has been incorporated into a microsphere. Microspheres (200 mg) are suspended in pH 7.2 phosphate-buffered saline (PBS) (2.5 ml) and agitated at 37 degrees C and 100 rpm in an environmental incubator shaker (G-24, New Brunswick Scientific Co., Edison, N.J.). At specific sampling times (each day for the first 4 days and every other day thereafter) the buffer solution is completely removed and replaced with fresh PBS. The peptide content of the PBS is measured using the Bradford method or other suitable quantitative assay typically used for protein analysis.

All the disclosed peptides may be synthesized using standard Fmoc (9-fluorenylmethoxycarbonyl) solid-phase chemistry on an Advanced ChemTech® Apex 396® Multiple Peptide Synthesizer. The Apex 396® is equipped with a 40-well reaction block for the production of up to 40 peptides simultaneously at a scale of 0.15 mmol. The peptides can be prepared as either amidated or free acid sequences using standard amino acids. The resin was first washed and pre-swelled with N,N-dimethyl formamide (DMF). The swelling time was one hour for Rink amide resins. The Fmoc protecting group was removed with 25% piperidine in DMF for 25 minutes, after which the piperidine was completely washed from the resin. To control racemization processes, the Fmoc amino acid monomers were pre-activated in an equimolar solution of 1-hydroxy-benzotriazole (HOBt) or 1-hydroxy-7-aza-benzotriazole (HOAt) in DMF at a 0.5 M concentration. The amide couplings were carried out using O-(7-azabenzotriazol-1-yl)-1,1,3,3-tetramethyluronium hexafluorophosphate (HATU) PyBop® or 2-(1H-benzotriazol-1-yl-)-1,1,3,3-tetrameth-yluronium hexafluorophosphate (HBTU) as an activation agent and 2.5-5.0 fold molar excess of amino acid under basic conditions using a hindered base (diisopropylethylamine). The coupling times were 1-1.5 hours followed by a wash and re-coupling to accomplish a double or triple couple before deprotection and continuation of the growing peptide chain. Coupling efficiency was monitored using the standard Kaiser test. Once the peptide synthesis was completed on the resin, the final Fmoc group was removed as above and the sequences were left as the free base.

Cleavage of the acid-labile linkage of the peptide to the resin was accomplished using 95% trifluoroacetic acid (TFA) and water with the appropriate scavengers added. After cleavage was allowed to proceed for about 30 minutes to one hour, the released peptides were immediately removed from the cleavage block and transferred to tubes for the removal of the TFA under reduced pressure. The peptides were then ready for purification and analysis via high performance liquid chromatography (HPLC) using a reverse phase C18 column and mass spectrometry. Primary sequence confirmation and preparative purification was accomplished using an LC/MS/MS system (ABI API2000).

General to the above protocol, the peptides may be produced using any method known to those skilled in the art such as those disclosed in Merrifield, R. B., *Solid Phase Peptide Synthesis I.*, J. AM. CHEM. SOC. 85:2149-2154 (1963); Carpino, L. A. et al., *[(9-Fluorenylmethyl)Oxy]Carbonyl (Fmoc) Amino Acid Chlorides: Synthesis, Characterization, And Application To The Rapid Synthesis Of Short Peptides*, J. ORG. CHEM. 37:51:3732-3734; Merrifield, R. B. et al., *Instrument For Automated Synthesis Of Peptides*, ANAL. CHEM. 38:1905-1914 (1966); or Kent, S. B. H. et al., *High Yield Chemical Synthesis Of Biologically Active Peptides On An Automated Peptide Synthesizer Of Novel Design*, IN: PEPTIDES 1984 (Ragnarsson U., ed.) Almqvist and Wiksell Int., Stockholm (Sweden), pp. 185-188, all of which are incorporated by reference herein in their entirety. Preferably, the peptides will be produced by a machine capable of sequential addition of amino acids to a growing peptide chain. However, the peptides may also be manufactured using standard solution phase methodology, which can be amenable to large-scale production efforts.

Methods of Use

Additional embodiments of the current invention are directed towards methods of using the above-described peptides, such as in formulations or as therapeutic agents. These methods may involve the use of a single peptide, or multiple peptides in combination.

The peptides of the current invention may be used for treating wounds of the skin (epidermis, dermis and hypodermis) and associated mucosal tissues. As used herein, the term "associated mucosal tissues" relates to any tissue organized in a manner similar to the skin and contains epithelial cells. Keratinocytes are a non-limiting example of such epithelial cells. Examples of such tissues are oral, nasopharyngeal, aural and urogenital surfaces, as well as the palpebral conjunctiva of the eye. Other examples of associated mucosal tissues include the entire lining (i.e. lumen) of the alimentary canal, including the esophagus, stomach, small intestine, large intestine (colon), and rectum. These latter examples can sustain wounds/lesions much like those that can affect the skin, and as such can be targeted with the present invention. Examples of wounds/lesions/injuries that can affect these tissues and are amenable to treatment with the inventive peptides are abrasions, blisters, burns, lacerations, punctures, ulcers, bruises, rashes and scars. Post-surgical tissue trauma can also be treated with the peptides.

The inventive peptides may also be used to prevent or reverse the effects of aging on all of the abovementioned tissues. In a related manner, the peptides could be applied to tissue that has been damaged by exposure to various external agents such as sunlight. Examples of debilitation related to aging and exposure are skin wrinkling, dryness, thinning, sagging and greater susceptibility to bruising. The invention can also be used as a cosmetic in these regards to render a more youthful appearance and texture, and to provide better function.

Other tissue problems that are effectively treated using the peptides of the present invention are related to allergy or autoimmunity. Such maladies include dermatitis, psoriasis, scleroderma, pemphigus and inflammatory bowel disease.

The compositions used to deliver the peptides in the above therapeutic method can be an aerosol, emulsion, liquid, lotion, cream, paste, ointment, powder, or foam, or other pharmaceutically acceptable formulation. Furthermore, the peptides can be delivered using less involved formulations such as deionized/distilled water, PBS or standard medical saline solutions. Generally, a pharmaceutically acceptable formulation would include any carrier suitable for use on human skin. Such pharmaceutically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. The concentration of the peptide in the composition can be about 0.1 µg/mL to about 50 µg/mL or about 0.1 µg/mL to about 20 µg/mL; however, the ultimate concentration employed may vary outside these ranges, depending on the nature of the wound/tissue condition, the bio-activity of the inventive peptide and the use of any adjuvant or technique to obtain enhanced composition absorption.

The compositions of the present invention can contain one or more additional agents that exert skin care activity.

In a preferred embodiment of the instant invention, where the composition is to be in contact with human keratinous tissue, any additional components besides the inventive peptides should be suitable for application to keratinous tissue; that is, when incorporated into the composition, such other components demonstrate undue toxicity, incompatibility, instability, allergic response, and the like within the scope of sound medical judgment. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/ colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, cosmetic biocides, denaturants, drug astringents, external analgesics, film formers or materials, opacifying agents, pH adjusters, propellants, reducing agents, sequestrants, skin bleaching and lightening agents (e.g. hydroquinone, kojic acid, ascorbic acid, magnesium ascorbyl phosphate, ascorbyl glucosamine), skin-conditioning agents (e.g. humectants), skin soothing and/or healing agents (e.g. panthenol and its derivatives, aloe vera, pantothenic acid and its derivatives, allantoin, bisabolol, and dipotassium glycyrrhizinate), skin treating agents, thickeners, and vitamins and derivatives thereof.

The administration of the inventive peptides and associated compositions may be made to humans and animals, including all mammals. Application may also be made in combination with typical and/or experimental materials such as tissue grafts, tissue culture products, oxygen and dressings. In general, the composition can be administered topically, orally, transdermally, systemically, or by any other method known to those of skill in the art to be useful to deliver the inventive peptides to the injury site. Compositions may also be applied in an in vitro or ex vivo manner, either to cells or patient grafts growing in culture, for example.

Due to their small size, the peptides are expected to be able to gain by themselves some level of permeability through the skin; however, certain techniques may be used to amplify this movement. For example, lipophilic (non-polar) groups can be added to the peptides, or the peptides can be delivered to the skin in a lipophilic excipient, in order to enhance peptide accessibility to the stratum corneum to allow translocation to the lower epidermal layers. In this manner such lipophilic modifications may be considered as a pro-drug. Permeation enhancers such as known solvents and surfactants may be used in the excipient to allow better peptide absorption. Special techniques that are anticipated to be useful in enhancing peptide access to the targeted tissue/injury include iontophoresis, electrophoresis and ultrasound. An iontophoretic device consists of two electrodes immersed in an electrolyte solution and placed on the skin. When an electric current is applied across the electrodes, an electric field is created across the stratum corneum that drives the delivery of the peptides. Electroporation involves the application of high-voltage electric pulses to increase the permeation through lipid bilayers. This differs from iontophoresis in the duration and intensity of the application of electrical current (iontophoresis uses a relatively constant low-voltage electric field). The high-voltage electric pulse of electroporation is believed to induce a reversible formation of hydrophilic pores in the lipid lamellae membranes that can provide a high degree of permeation enhancement. Ultrasound applies sound waves having a frequency greater than 16 kHz to the skin, which causes compression and expansion of the tissue through which the sound waves travel. The resulting pressure variations cause a number of processes (e.g., cavitation, mixing, increase in temperature) that may enhance permeation of the peptides.

All the above peptide formulations and uses are well known in the art. Additional modes of preparing and using the inventive peptides are described, for example, in U.S. Pat. Nos. 6,492,326 and 6,974,799, both of which are incorporated herein by reference in their entirety.

The following examples are included to demonstrate certain preferred embodiments of the invention.

EXAMPLES

Example 1

Identification of Peptides that Stimulate Cell Proliferation

As the HB-107 (SEQ ID NO:1) peptide fragment has previously been shown to stimulate wound healing in vivo (Lee et al., 2004), it was hypothesized that within the sequence of HB-107 there may exist yet smaller peptide fragments that can similarly or better stimulate wound healing and related processes. To examine this question, an overlapping set of peptide fragments of HB-107 was generated using standard solid phase peptide chemistry. These peptides were then assayed for cell proliferation activity at concentrations of 0.22, 2.15, 21.5 and 46.4 µg/mL. A number of peptides caused a significant increase in the proliferation of epidermal keratinocytes at low concentrations (Table 2), including peptides HB-1061 (SEQ ID NO:3) and HB-1072 (SEQ ID NO:6) which, respectively, only contain seven and six amino acids each. Several other peptides exhibited stimulatory activity at levels equal to or above that of HB-107 (Table 2). In conclusion, the cell proliferation induced by a number of the inventive peptides exceeded the level induced by the parent HB-107 peptide. Importantly, several of these fragments are significantly shorter than HB-107.

TABLE 2

Induction of PAM 212 murine epidermal keratinocyte proliferation by the inventive peptides. Values represent cell proliferation as a percent of control cell proliferation (cells treated with PBS only). Bolded values indicate proliferation levels exceeding 150% of control cell proliferation.

| SEQ ID NO: | Peptide | 0.22 µg/mL | 2.15 µg/mL | 21.5 µg/mL | 46.4 µg/mL |
|---|---|---|---|---|---|
| 1 | HB-107 | 57 | 75 | 121 | 126 |
| 12 | HB-802 | 121 | 130 | 135 | 133 |
| 11 | HB-801 | 101 | 100 | 113 | 131 |
| 10 | HB-912 | 100 | 84 | 125 | 137 |
| 7 | HB-1074 | 97 | 93 | 120 | 149 |
| 5 | HB-1071 | 106 | 127 | 188 | 155 |
| 13 | HB-1056 | 48 | 39 | 64 | 97 |
| 9 | HB-1057 | 121 | 118 | 171 | 167 |
| 6 | HB-1072 | 98 | 107 | 185 | 237 |
| 2 | HB-1059 | 95 | 128 | 162 | 186 |
| 14 | HB-1060 | 57 | 52 | 90 | 83 |
| 3 | HB-1061 | 122 | 156 | 163 | 241 |

The cell proliferation assays proceeded from the following experimental protocol:

Cell Proliferation Assay Using a Mouse Keratinocyte Cell Line.

OBJECTIVE: To determine the anti-proliferative or cytotoxic potential of a test article when applied to epidermal keratinocytes in culture.

TEST SYSTEM: Either the murine keratinocyte cell line PAM212 or primary Normal Human Epidermal Keratinocytes (NHEK, from Clonetics) are preferred models, although other cells may be used.

Reagents:

1. Cell growth media: Dulbecco's Modified Eagles Medium containing 10% newborn calf serum (DMEM-10), penicillin (100 units/mL), streptomycin (0.1 mg/mL), and gentamicin (50 µg/mL) or Keratinocyte Growth Medium (KGM, from Clonetics) for human cells.

2. Vehicle media: Dulbecco's Modified Eagles Medium containing 1.0% newborn calf serum (DMEM-1), penicillin (100 units/mL), and streptomycin (0.1 mg/mL) or Keratinocyte Basal Medium (KBM, from Clonetics) for human cells.

3. Neutral red stock solution: neutral red powder is added to Dulbecco's Phosphate Buffered Saline (DPBS) at a concentration of 3 mg/mL. The resulting solution is then sterile-filtered.

4. Neutral red media: neutral red stock solution is added to DMEM or KBM at a final concentration of 50 µg/mL.

5. MTT media: MTT (3-(4,5-dimethylthiazol-2-yl)-2,5-diphenyltetrazolium bromide) powder is added to DMEM or KBM at 1 mg/mL and filtered or centrifuged to remove any precipitate. MTT solution is used within 24 hours.

6. Fixing solution consisting of 1% formaldehyde and 1% calcium chloride in an aqueous solution.

7. Washing solution consisting of PBS.

8. Lysing solution: 1.0% glacial acetic acid and 50% ethanol in an aqueous solution for neutral red, or acidified isopropanol for MTT-treated cells.

Cell Plating:

Keratinocytes are examined microscopically daily. As the culture becomes 50-75% confluent, the media in the plate is aspirated and 0.25% trypsin/EDTA is added (0.05% trypsin for human cells). When the cells become rounded, the trypsin is neutralized by addition of an equal volume of DMEM or KBM supplemented with approximately 10% bovine serum or by using trypsin neutralizing solution (TNS, from Clonetics). Cells are then centrifuged and the pellet is resuspended in 1 ml of DMEM-1 or KBM. A hemacytometer is used to count the cell suspension and the total number of cells/mL is adjusted to $1.5$-$2.5 \times 10^4$ cells/mL with DMEM-1 or KBM. Cells are then plated in 96-well plates at a concentration of $3.0$-$5.0 \times 10^3$ cells/well by adding 200 µL of the cell suspension to each well. Typically, the central 60 wells are used and the outer wells are filled with DMEM or PBS to minimize evaporation effects.

Sample Preparation:

A stock solution of the test article is prepared using DMEM-1 or KBM, and all other dilutions are henceforth prepared from this solution. Typically, each dilution is filtered through an 0.2-µm filter before application to the cell culture. A 1.0% (w/v or v/v) solution or suspension is prepared, and 10-fold or 3-fold serial dilutions are made in culture medium.

Dosing:

The cells are examined 18-24 hours after plating to ensure cell attachment and division, and then 100 µL of the media is aspirated, leaving behind 100 µL in each well. Then 100 µL of a 2× concentration of each test article dilution is added to the replicate wells. For the negative control, 100 µL of the vehicle media (DMEM-1 or KBM) is added to the control wells. The microplate is then incubated at 37 degrees C. and 5.0% $CO_2$ for 48-72 hours after dosing, and cells are allowed to proliferate undisturbed. Following this 48-72 hour exposure, all media is aspirated and proliferation is assessed by one of the below methods.

Option A: neutral red uptake. After exposure and aspiration of media, 200 μL of neutral red media is immediately added to each well. The microplate is returned to the incubator for an additional three hours. Following this dye uptake period, the microplate is removed from the incubator and gently inverted, and the neutral red media is decanted into a collection pan. The cells are then fixed with fixing solution for approximately one minute. The fixing solution is decanted off, and the microplate is washed gently three times with washing solution. The washing solution is decanted, and 200 μL of lysing solution is added. After at least 15 minutes, the contents of each well are re-pipetted to ensure even color distribution in each well, and an aliquot is read on the spectrophotometer as detailed below.

Option B: MTT conversion assay. After exposure and aspiration of media, 200 μL of MTT assay media is immediately added to each well. (MIT should be used only if the test article does not reduce MIT directly, as determined by a range-finding experiment or MIT compatibility test). The microplate is returned to the incubator for an additional three hours. Following this dye uptake period, the microplate is removed from the incubator and gently inverted, and the MTT media is decanted into a collection pan. The cells are then washed gently three times with washing solution. The washing solution is decanted, and 200 μL of lysing solution is added. After lysing for at least 60 minutes, each well is re-pipetted to ensure even color distribution in each well, and the absorbance is read on the spectrophotometer as detailed below.

Option C: Flow cytometry-based analyses. After exposure, the medium is adjusted to 10 μM bromodeoxyuridine (BrdU) and incubated at 37 degrees C. for 45 minutes. During this incubation, BrdU, a thymidine analog, is incorporated into the DNA of proliferating cells. The cells are then be harvested by trypsinization. Following centrifugation, the cell pellet is resuspended in 0.5 ml of PBS and the cells are fixed by the addition of 70% ethanol. The cells are then be washed and stained with the DNA-specific (red) fluorescent dye propidium iodide. The proliferating cells are stained with a BrdU-specific fluorescent (green) antibody. Cell cycle analysis as well as the amount of proliferating cells staining positive for BrdU is determined using flow cytometry. (Note: for flow cytometry studies, cells are cultured in 24-well or 6-cm plates).

Analysis of Data

Dye Uptake Studies: For dye-based endpoints the optical density of the wells is read using a Titertek Multiskan® MCC/340 at a wavelength of 540 nm subtracting the absorbance at a reference wavelength of 620 nm for neutral red, or 670 nm to 680 nm reference wavelength for MIT. A printout of the absorbance values is generated by the plate reader. The average absorbance and standard deviations are calculated for each treatment group, and the results are expressed as percent of control absorbencies. EC50 Calculation: The data is plotted as percent of control absorbencies vs. concentrations for each test sample. The EC50 is extrapolated from the regression line drawn through the data in an Excel 5.0 graph. In addition, the EC50 is calculated using the equation for the regression line provided by the Excel 5.0 graph or by using an Excel 5.0 macro.

Flow Cytometry Studies: For flow cytometric analysis the percent positive BrdU-labeled will be determined and a proliferation index (i.e., % of cells actively proliferating at time of harvest) will be calculated. Optionally, other parameters such as percent cell viability and the percentage of apoptotic cells in the samples can also be determined.

Example 2

Identification of Peptides that Stimulate Cell Migration

Cell proliferation alone is not sufficient to aid in wound healing. Upon sustaining an injury, cells bordering the wound proliferate; the migration of such newly formed cells to close the injury (or chronic lesion of older, dysfunctional tissue) is of equal importance. To address this issue, HB-107 and peptide fragments thereof were examined using a keratinocyte cell migration assay based on a simple tissue culture scratch test. This assay demonstrated that peptides such as HB-1072 (SEQ ID NO:6) and HB-1061 (SEQ ID NO:3) are capable of increasing the migration of cells in a manner similar to that of the parent HB-107 peptide (Table 3). It is of interest to note that the HB-1072 and HB-1061 peptides overlap as part of HB-107, and that the analog HB-1062 (SEQ ID NO:4) exhibits no migratory activity on cells. The protocol for this assay is standard and has been described by Shanley et al. (2004, *Invest. Ophthalmol. Vis. Sci.* 45:1088-1094), the article of which is herein incorporated by reference in its entirety.

TABLE 3

Induction of human epidermal keratinocyte migration by the inventive peptides, as measured by a scratch test. Values represent percent closure of the scratch compared to initial width of the scratch to cell monolayer, after 6 or 10 hours exposure to peptide.

| SEQ ID NO: | Peptide | 6 hr | 10 hr |
|---|---|---|---|
| NA | PBS control | 11 | 33 |
| 1 | HB-107 | 52 | 78 |
| 6 | HB-1072 | 55 | 77 |
| 3 | HB-1061 | 44 | 67 |
| 4 | HB-1062 | 0 | 24 |

Example 3

Identification of Peptides that Stimulate Anti-inflammatory Activity in Resting Cells In addition to increasing the rate of healing, peptide HB-107 has also been shown to decrease the level of inflammation associated with a wound. To identify small peptide fragments that may exhibit such an activity, fragments of HB-107 were screened for the activity of reducing a key inflammatory cytokine, IL6. It was found that peptide fragments HB-802 (SEQ ID NO:12) and HB-1076 (SEQ ID NO:8) decrease the level of IL6 expression to the same degree as the HB-107 parent peptide (Table 4). The protocol for this assay is standard and described by Murakami et al. (2004, *J. Immunol.* 172:3070-3037), the article of which is incorporated herein by reference in its entirety.

TABLE 4

Repression of IL6 expression in epithelial cells exposed to the inventive peptides. The amount of IL6, expressed in pg/mL (columns 3-5), was determined 24 and 48 hours after addition of media containing 20 μg/mL peptide. Percent change in IL6 expression is given in column 8.

| SEQ ID NO: | Test | Well 1 | Well 2 | Average | SD | Change | % Change |
|---|---|---|---|---|---|---|---|
| | | | | 24 hr | | | |
| | PBS control | 334.26 | 292.09 | 313.175 | 21.085 | NA | NA |
| | PBS control | 311.02 | 335.98 | 323.5 | 12.48 | NA | NA |
| | PBS control | 319.63 | 349.75 | 334.69 | 15.06 | NA | NA |
| 12 | HB-802 | 278.32 | 288.65 | 283.485 | 5.165 | −40.435 | −12.50% |
| 1 | HB-107 | 307.58 | 264.55 | 286.065 | 21.515 | −37.435 | −11.60% |
| 8 | HB-1076 | 278.32 | 255.08 | 266.7 | 11.62 | −56.8 | −17.60% |
| | | | | 48 hr | | | |
| | PBS control | 1049.2 | 1007.3 | 1028.25 | 20.95 | NA | NA |
| | PBS control | 927.27 | 1022.8 | 975.035 | 47.765 | NA | NA |
| | PBS control | 1002.1 | 904.89 | 953.495 | 48.605 | NA | NA |
| 12 | HB-802 | 774.07 | 762.02 | 768.045 | 6.025 | −206.99 | −21.20% |
| 1 | HB-107 | 690.58 | 786.12 | 738.35 | 47.77 | −236.685 | −24.30% |
| 8 | HB-1076 | 726.73 | 728.45 | 727.59 | 0.86 | −247.445 | −25.40% |

Example 4

Identification of Peptides that Inhibit Ultraviolet-B (UVB)-induced Inflammatory Activity in Cells Given that certain small peptides were able to promote anti-inflammatory activity in resting cells (see Example 3), it was of interest to know whether small peptides could promote such activity in cells that were exposed to UVB radiation. UVB radiation damages skin and promotes aging thereof. Since inflammation in damaged tissue is a contributor to aging in that tissue, reduction of epidermal inflammation resulting from ultraviolet light-induced damage will lessen the aging effects thereof.

Figure 1:
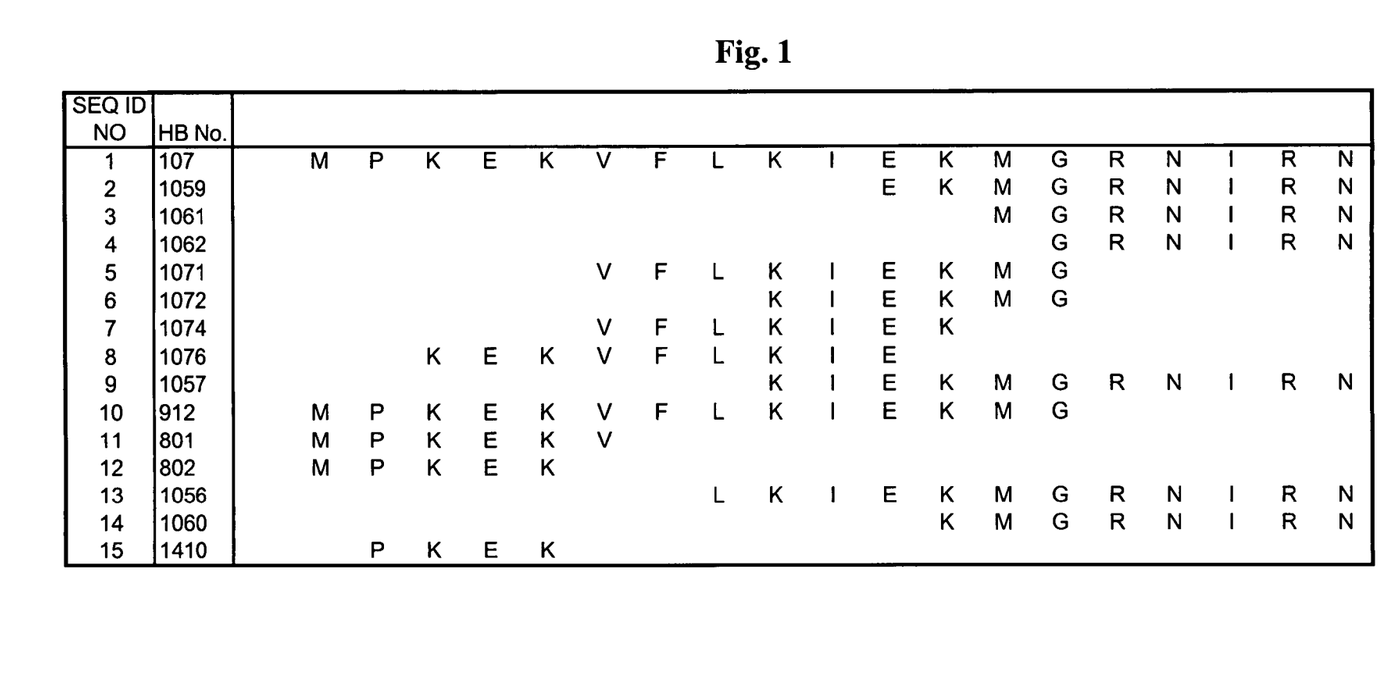
FIG. 1: The inventive peptides are shown as they align with the parent peptide HB-107 (SEQ ID NO:1).
Figure 2:
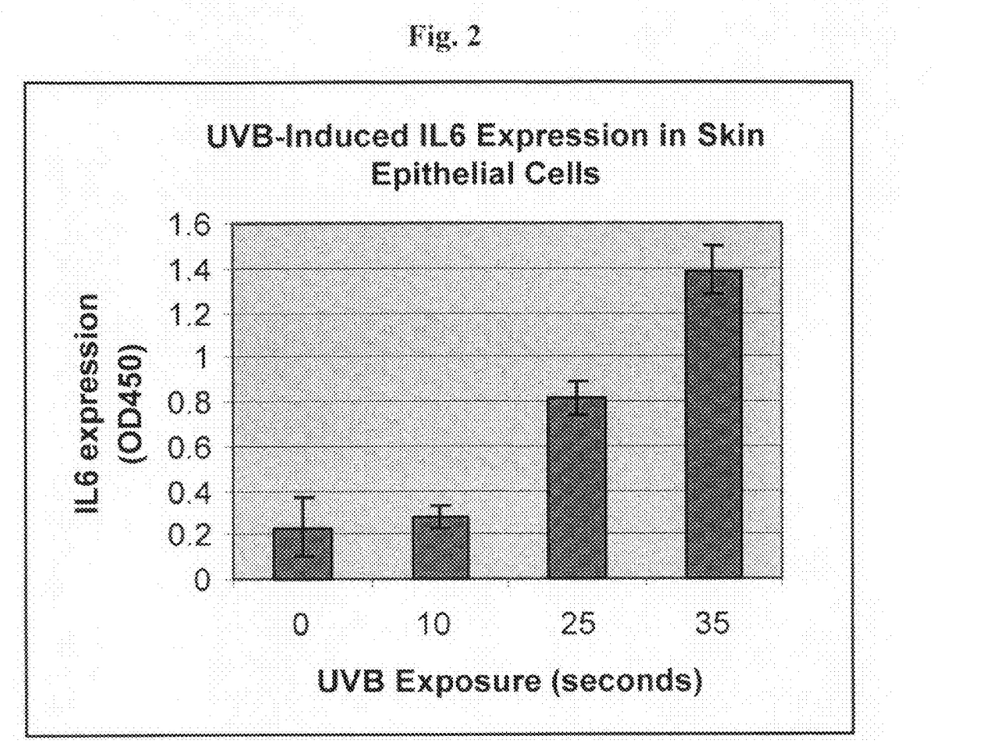
FIG. 2: IL6 expression by skin epithelial cells in response to ultraviolet-B (UVB) light exposure. Cells were exposed to UVB irradiation for certain time periods (0-35 seconds) and IL6 expression was measured by ELISA twenty-four hours post-UVB irradiation. Each treatment was performed in triplicate. Refer to Example 4.

An assay was performed to determine whether peptide fragments of HB-107 can induce anti-inflammatory activity in cells exposed to ultraviolet light. Human skin epithelial cells (ATCC CRL-2592) were seeded into 6-well plates and grown to more than 95% confluence in DMEM with 4 mM L-glutamine adjusted to contain 1.5 g/L sodium bicarbonate and 4.5 g/L glucose (complete medium) supplemented with 10% fetal bovine serum. The cells were serum starved for 5 hours prior to UVB treatment. UVB was generated using a UVLMS lamp (4W model, 3UV assembly, Upland, Calif.) with the irradiation wavelength set at 302 nm. The UV lamp was placed 12 cm above the tissue culture plate (6-well plate) and two wells were treated at one time to allow homogenous UVB irradiation. Cells were exposed to UVB irradiation (450 μW/cm$^2$, measured using a radiometer) in PBS to avoid ultraviolet light-induced generation of toxic photochemicals. IL6 expression was measured as an indicator of cell inflammatory activity in response to UVB. As shown in FIG. 2, IL6 expression in skin epithelial cells was induced in a UVB dose-dependent manner, thus demonstrating that ultraviolet light stimulates cellular inflammatory processes in skin epithelial cells.

Figure 3:
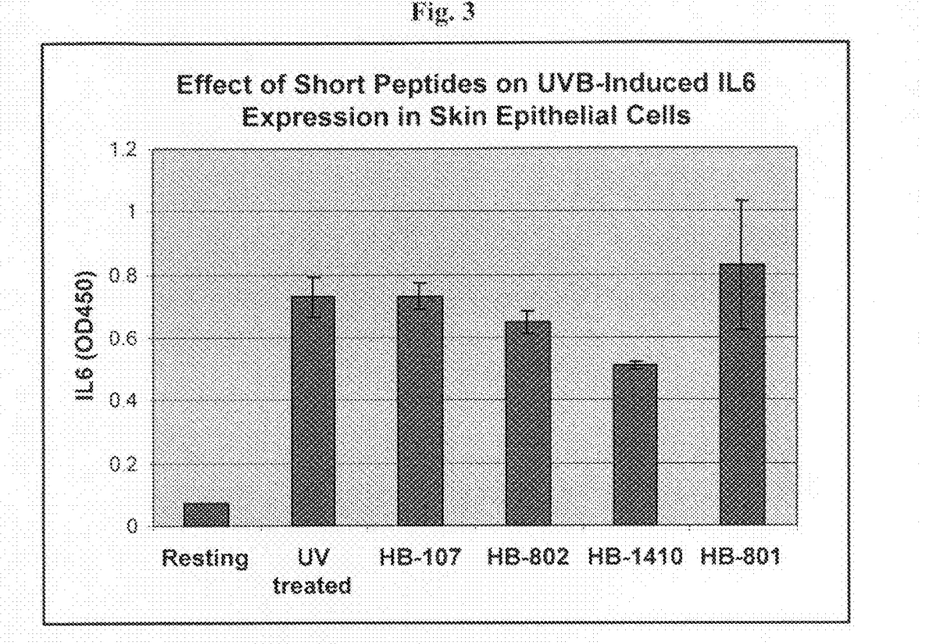
FIG. 3: Effect of short peptides on UVB-induced IL6 expression in skin epithelial cells. Cells were exposed to UVB irradiation for 35 seconds, after which cells were incubated in complete medium (no serum) with 40 µg/mL peptide [HB-107 (SEQ ID NO:1), HB-802 (SEQ ID NO:12), HB-1410 (SEQ ID NO:15), HB-801 (SEQ ID NO:31)] for twenty hours. IL6 expression was then measured by ELISA. Refer to Example 4.

Individual peptides were screened to determine the effects thereof on UVB-induced IL6 expression in skin epithelial cells. Cells were exposed to UVB (450 μW/cm$^2$) for 35 seconds in PBS, after which the PBS was replaced with complete medium without serum in the presence or absence of 40 μg/ml peptide and incubated at 37 degrees C./5% CO$_2$ for twenty hours. The supernatant media was then collected and centrifuged at 10,000 rpm to remove debris, prior to ELISA for human IL6 (CellSciences, Mass.). It was found that specific sequences within the HB-107 peptide are capable of significantly reducing IL6 expression in cells subjected to a potent inflammatory stimulus (Table 5, results shown graphically in FIG. 3).

TABLE 5

Effect of short peptides on UVB-induced IL6 expression in skin epithelial cells. Cells were exposed to UVB followed by incubation with peptide. Control cells received neither UVB or peptide treatment. IL6 expression was measured by ELISA using a light spectrometer (OD 450).

| SEQ ID NO | UV/peptide Treatment | IL6 (OD 450) | SD |
|---|---|---|---|
| | Control | 0.0730 | 0.001414 |
| | UV only | 0.7305 | 0.062933 |
| 1 | HB-107 | 0.7315 | 0.043134 |
| 12 | HB-802 | 0.6500 | 0.035423 |
| 15 | HB-1410 | 0.5105 | 0.013435 |
| 11 | HB-801 | 0.8275 | 0.204354 |

The results from this study show that peptides such as HB-1410 (PKEK, SEQ ID NO:15) are capable of significantly reducing the level of IL6 produced by skin epithelial cells in response to UV radiation. This activity is of particular application to skin care after sun exposure, and also has broad application toward reducing associated inflammation in a variety of skin conditions resulting from wounds and aging. It is interesting to note that even minor changes in the peptide sequence can significantly alter peptide inhibitory activity towards IL6 expression in skin epithelial cells [e.g. compare activities of HB-801 (PKEKV) and HB-802 (MPKEK) with the inhibitory activity of HB-1410]. Interestingly, HB-802 has demonstrated the ability to reduce IL6 in resting cells (refer to Example 3, Table 4).

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

REFERENCES

Braff M H, Gallo R L (2006). Antimicrobial peptides: an essential component of the skin defensive barrier. *Curr. Top. Microbiol. Immunol.* 306:91-110.

Enoch S, Price P (2004). Cellular, molecular and biochemical differences in the pathophysiology of healing between acute wounds, chronic wounds and wounds in the aged. *World Wide Wounds*. Online: www.worldwidewounds.com.

Fisher G J, Kang S, Varani J, Bata-Csorgo Z, Wan Y, Datta S, Voorhees J J (2002). Mechanisms of photoaging and chronological skin aging. *Arch. Dermatol.* 138:1462-1470.

Kyte J, Doolittle R F (1982). A simple method for displaying the hydropathic character of a protein. *J. Mol. Biol.* 157:105-132.

Lee P H, Rudisill J A, Lin K H, Zhang L, Harris S M, Falla T J, Gallo R L (2004). HB-107, a nonbacteriostatic fragment of the antimicrobial peptide cecropin B, accelerates murine wound repair. *Wound Repair Regen.* 12:351-358.

Liechty K W, Adzick N S, Crombleholme T M (2000). Diminished interleukin 6 (IL-6) production during scarless human fetal wound repair. *Cytokine.* 12:671-676.

Martin P, Leibovich S J (2005). Inflammatory cells during wound repair: the good, the bad and the ugly. *Trends Cell Biol.* 15:599-607.

Mustoe T A, Cutler N R, Allman R M, Goode P S, Deuel T F, Prause J A, Bear M, Serdar C M, Pierce G F (1994). A phase II study to evaluate recombinant platelet-derived growth factor-BB in the treatment of stage 3 and 4 pressure ulcers. *Arch. Surg.* 129:213-219.

Oyama N, Sekimata M, Nihei Y, Iwatsuki K, Homma Y, Kaneko F (1998). Different growth properties in response to epidermal growth factor and interleukin-6 of primary keratinocytes derived from normal and psoriatic lesional skin. *J. Dermatol. Sci.* 16:120-128.

Pelicci P G (2004). Do tumor-suppressive mechanisms contribute to organism aging by inducing stem cell senescence? *J. Clin. Invest.* 113:4-7.

Presland R B, Dale B A (2000). Epithelial structural proteins of the skin and oral cavity: function in health and disease. *Crit. Rev. Oral Biol. Med.* 11:383-408.

Sato S, Hasegawa M, Takehara K (2001). Serum levels of interleukin-6 and interleukin-10 correlate with total skin thickness score in patients with systemic sclerosis. *J. Dermatol. Sci.* 27:140-146.

Shaykhiev R, Beisswenger C, Kandler K, Senske J, Puchner A, Damm T, Behr J, Bals R (2005). Human endogenous antibiotic LL-37 stimulates airway epithelial cell proliferation and wound closure. *Am J. Physiol. Lung Cell Mol. Physiol.* 289:L842-L848.

Steed D L (1995). Clinical evaluation of recombinant human platelet-derived growth factor for the treatment of lower extremity diabetic ulcers. Diabetic Ulcer Study Group. *J. Vasc. Surg.* 21:71-78.

Sugawara T, Gallucci R M, Simeonova P P, Luster M I (2001). Regulation and role of interleukin 6 in wounded human epithelial keratinocytes. *Cytokine.* 15:328-336.

Sweitzer S M, Fann S A, Borg T K, Baynes J W, Yost M J (2006). What is the future of diabetic wound care? *Diabetes Educ.* 32:197-210.

Zhang L, Falla T J (2006). Antimicrobial peptides: therapeutic potential. *Expert Opin. Pharmacother.* 7:653-663.

What is claimed is:

1. An isolated peptide compound, wherein the sequence of the peptide is SEQ ID NO:2, SEQ ID NO:3, SEQ ID NO:5, SEQ ID NO:7, SEQ ID NO:8, SEQ ID NO:9, SEQ ID NO:10, SEQ ID NO: 11, SEQ ID NO:12, or SEQ ID NO:15; wherein the amino acid residues of the peptide are optionally D-amino acids; and wherein the peptide is optionally amidated, lipidated, or conjugated to a carrier molecule.

2. The peptide of claim 1, wherein the peptide is conjugated to a carrier molecule, amidated or lipidated.

3. The peptide of claim 1, wherein the sequence of the peptide is SEQ ID NO:3, SEQ ID NO:10, SEQ ID NO:11, SEQ ID NO:12, or SEQ ID NO:15.

4. The peptide of claim 1, wherein the sequence of the peptide is SEQ ID NO:3, SEQ ID NO:12, or SEQ ID NO:15.

5. The peptide of claim 1, wherein the sequence of the peptide is SEQ ID NO:3.

6. The peptide of claim 1, wherein the sequence of the peptide is SEQ ID NO:12.

7. The peptide of claim 1, wherein the sequence of the peptide is SEQ ID NO:15.

8. A composition comprising at least one peptide according to claim 1 and a pharmaceutically acceptable carrier.

9. The composition of claim 8, wherein the peptide is present in a concentration ranging from about 0.1 μg/mL to about 50 μg/mL.

10. The composition of claim 8, wherein the peptide is present in a concentration ranging from about 0.1 μg/mL to about 20 μg/mL.

11. The composition of claim 8, wherein the composition is in the form of an aerosol, emulsion, liquid, lotion, cream, paste, ointment, powder or foam.

12. A method for healing a wound in a mammal, the method comprising administering to the wound of said mammal a therapeutically effective amount of the composition according to claim 8 for an effective amount of time.

13. The method of claim 12, wherein the wound affects the skin or associated mucosal tissue of said mammal.

14. The method of claim 12, wherein the wound is due to an abrasion, blister, burn, laceration, ulcer, bruise, rash, scar, or the effects of aging or environmental exposure.

15. The method of claim 12, wherein the therapeutically effective amount of the composition comprises peptide at a concentration ranging from about 0.1 μg/mL to about 50 μg/mL.

16. The method of claim 12, wherein the sequence of the peptide of the composition is SEQ ID NO:3.

17. The method of claim 12, wherein the sequence of the peptide of the composition is SEQ ID NO:12.

18. The method of claim 12, wherein the sequence of the peptide of the composition is SEQ ID NO:15.

* * * * *

SEQUENCE LISTING

```
<160> NUMBER OF SEQ ID NOS: 15

<210> SEQ ID NO 1
<211> LENGTH: 19
<212> TYPE: PRT
<213> ORGANISM: Hyalophora cecropia

<400> SEQUENCE: 1

Met Pro Lys Glu Lys Val Phe Leu Lys Ile Glu Lys Met Gly Arg Asn
1               5                   10                  15

Ile Arg Asn

<210> SEQ ID NO 2
<211> LENGTH: 9
<212> TYPE: PRT
<213> ORGANISM: Hyalophora cecropia

<400> SEQUENCE: 2

Glu Lys Met Gly Arg Asn Ile Arg Asn
1               5
```

```
<210> SEQ ID NO 3
<211> LENGTH: 7
<212> TYPE: PRT
<213> ORGANISM: Hyalophora cecropia

<400> SEQUENCE: 3

Met Gly Arg Asn Ile Arg Asn
1               5

<210> SEQ ID NO 4
<211> LENGTH: 6
<212> TYPE: PRT
<213> ORGANISM: Hyalophora cecropia

<400> SEQUENCE: 4

Gly Arg Asn Ile Arg Asn
1               5

<210> SEQ ID NO 5
<211> LENGTH: 9
<212> TYPE: PRT
<213> ORGANISM: Hyalophora cecropia

<400> SEQUENCE: 5

Val Phe Leu Lys Ile Glu Lys Met Gly
1               5

<210> SEQ ID NO 6
<211> LENGTH: 6
<212> TYPE: PRT
<213> ORGANISM: Hyalophora cecropia

<400> SEQUENCE: 6

Lys Ile Glu Lys Met Gly
1               5

<210> SEQ ID NO 7
<211> LENGTH: 7
<212> TYPE: PRT
<213> ORGANISM: Hyalophora cecropia

<400> SEQUENCE: 7

Val Phe Leu Lys Ile Glu Lys
1               5

<210> SEQ ID NO 8
<211> LENGTH: 9
<212> TYPE: PRT
<213> ORGANISM: Hyalophora cecropia

<400> SEQUENCE: 8

Lys Glu Lys Val Phe Leu Lys Ile Glu
1               5

<210> SEQ ID NO 9
<211> LENGTH: 11
<212> TYPE: PRT
<213> ORGANISM: Hyalophora cecropia

<400> SEQUENCE: 9

Lys Ile Glu Lys Met Gly Arg Asn Ile Arg Asn
1               5                   10

<210> SEQ ID NO 10
<211> LENGTH: 14
```

```
<212> TYPE: PRT
<213> ORGANISM: Hyalophora cecropia

<400> SEQUENCE: 10

Met Pro Lys Glu Lys Val Phe Leu Lys Ile Glu Lys Met Gly
1               5                   10

<210> SEQ ID NO 11
<211> LENGTH: 5
<212> TYPE: PRT
<213> ORGANISM: Hyalophora cecropia

<400> SEQUENCE: 11

Pro Lys Glu Lys Val
1               5

<210> SEQ ID NO 12
<211> LENGTH: 5
<212> TYPE: PRT
<213> ORGANISM: Hyalophora cecropia

<400> SEQUENCE: 12

Met Pro Lys Glu Lys
1               5

<210> SEQ ID NO 13
<211> LENGTH: 12
<212> TYPE: PRT
<213> ORGANISM: Hyalophora cecropia

<400> SEQUENCE: 13

Leu Lys Ile Glu Lys Met Gly Arg Asn Ile Arg Asn
1               5                   10

<210> SEQ ID NO 14
<211> LENGTH: 8
<212> TYPE: PRT
<213> ORGANISM: Hyalophora cecropia

<400> SEQUENCE: 14

Lys Met Gly Arg Asn Ile Arg Asn
1               5

<210> SEQ ID NO 15
<211> LENGTH: 4
<212> TYPE: PRT
<213> ORGANISM: Hyalophora cecropia

<400> SEQUENCE: 15

Pro Lys Glu Lys
1
```